United States Patent
Jang et al.

(10) Patent No.: US 10,206,577 B2
(45) Date of Patent: Feb. 19, 2019

(54) WEARABLE DEVICE AND HEALTH MONITORING METHOD

(71) Applicant: SAMSUNG ELECTRONCIS CO., LTD., Suwon-si (KR)

(72) Inventors: Hyeong Seok Jang, Gimcheon-si (KR); Hyun Seok Moon, Seoul (KR); Jae Wook Shim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 32 days.

(21) Appl. No.: 15/420,626

(22) Filed: Jan. 31, 2017

(65) Prior Publication Data

US 2018/0110413 A1    Apr. 26, 2018

(30) Foreign Application Priority Data

Oct. 26, 2016    (KR) .................. 10-2016-0140439

(51) Int. Cl.
| | | |
|---|---|---|
| *A61B 5/00* | (2006.01) | |
| *A61B 5/01* | (2006.01) | |
| *A61B 5/103* | (2006.01) | |

(52) U.S. Cl.
CPC .......... *A61B 5/0059* (2013.01); *A61B 5/015* (2013.01); *A61B 5/1032* (2013.01); *A61B 5/443* (2013.01);
(Continued)

(58) Field of Classification Search
CPC ..... A61B 5/015; A61B 5/0059; A61B 5/1032; A61B 5/443; A61B 5/444; A61B 5/6825; A61B 5/7278; A61B 5/7282; A61B 5/7405; A61B 5/742; A61B 5/7455; A61B 5/746; A61B 2562/0233; A61B 2562/043

USPC ........ 600/300–301, 372, 382–384, 386–390, 600/393, 407, 473–477, 479–480; 361/679.01–679.03

See application file for complete search history.

(56) References Cited

U.S. PATENT DOCUMENTS

| | | |
|---|---|---|
| 6,190,315 B1 | 2/2001 | Kost et al. |
| 7,003,337 B2 | 2/2006 | Harjunmaa et al. |

(Continued)

FOREIGN PATENT DOCUMENTS

| | | |
|---|---|---|
| JP | 2004226277 A | 8/2004 |
| JP | 201268263 A | 4/2012 |

(Continued)

OTHER PUBLICATIONS

G. L. Abbas, V. W. S. Chan, and T. K. Yee, "A dual-detector optical heterodyne receiver for local oscillator noise suppression," J. Lightwave Technol. 3(5), 1110-1122 (1985).

*Primary Examiner* — Gary Jackson
*Assistant Examiner* — Jonathan Kuo
(74) *Attorney, Agent, or Firm* — Sughrue Mion, PLLC

(57) ABSTRACT

A wearable device includes a body unit to be worn on a subject; a light source comprising a plurality of light emitting diodes and configured to emit light to the subject; a sensor comprising a plurality of photodiodes configured to generate electrical signals based on the light returning from the subject, the plurality of photodiodes being divided into a first photodiode (PD) group and a second PD group, and the photodiodes of the first PD group being disposed to face the photodiodes of the second PD group on the body unit; and a controller configured to extract biometric information of the subject based on the electrical signals generated by the plurality of photodiodes.

19 Claims, 10 Drawing Sheets

(52) U.S. Cl.
CPC ............ *A61B 5/444* (2013.01); *A61B 5/6825* (2013.01); *A61B 5/7278* (2013.01); *A61B 5/7282* (2013.01); *A61B 5/742* (2013.01); *A61B 5/7405* (2013.01); *A61B 5/746* (2013.01); *A61B 5/7455* (2013.01); *A61B 2562/0233* (2013.01); *A61B 2562/043* (2013.01)

(56) References Cited

U.S. PATENT DOCUMENTS

| | | |
|---|---|---|
| 7,066,884 B2 | 6/2006 | Custer et al. |
| 8,200,320 B2 | 6/2012 | Kovacs |
| 8,224,414 B2 | 7/2012 | Kellogg et al. |
| 8,287,483 B2 | 10/2012 | Mitragotri et al. |
| 8,870,810 B2 | 10/2014 | Mitragotri et al. |
| 2004/0171980 A1 | 9/2004 | Mitragotri et al. |
| 2006/0015058 A1 | 1/2006 | Kellogg et al. |
| 2006/0094944 A1 | 5/2006 | Chuang |
| 2006/0094945 A1 | 5/2006 | Barman et al. |
| 2008/0311670 A1 | 12/2008 | Zhu |
| 2012/0016231 A1 | 1/2012 | Westmoreland |
| 2014/0279528 A1 | 9/2014 | Slaby et al. |
| 2015/0248833 A1 | 9/2015 | Ame et al. |
| 2015/0277559 A1 | 10/2015 | Vescovi et al. |
| 2016/0066827 A1 | 3/2016 | Workman et al. |
| 2016/0077587 A1 | 3/2016 | Kienzle et al. |

FOREIGN PATENT DOCUMENTS

| | | |
|---|---|---|
| KR | 1020160007889 A | 1/2016 |
| KR | 101632583 B1 | 6/2016 |
| WO | 2014047205 A1 | 3/2014 | ns
WEARABLE DEVICE AND HEALTH MONITORING METHOD

CROSS-REFERENCE TO RELATED APPLICATION(S)

This application claims priority from Korean Patent Application No. 10-2016-0140439, filed on Oct. 26, 2016 in the Korean Intellectual Property Office, the disclosure of which is incorporated herein by reference in its entirety.

BACKGROUND

1. Field

Apparatuses and methods consistent with exemplary embodiments relate to monitoring a health status of a subject, and more particularly, to extracting biometric information of the subject from the hand of the subject.

2. Description of Related Art

In the past, personal health care services were centered on treatment of illness performed at hospitals or medical institutions. With the improvement of the standard of living and the growing interest in the quality of life and well-being, there is an increasing interest in the proactive health management services for healthy people which focus on the prevention of diseases through the measurement of health status.

To this end, research on a wearable device that is worn on a user's body to measure the user's health status has been actively conducted.

SUMMARY

According to an aspect of an exemplary embodiment, there is provided a wearable device comprising: a body unit configured to be worn on a subject; a light source comprising a plurality of light emitting diodes configured to emit light to the subject; a sensor comprising a plurality of photodiodes disposed on the body unit and configured to generate electrical signals based on the light returning from the subject, the plurality of photodiodes being divided into a first photodiode (PD) group and a second PD group, and the photodiodes of the first PD group being disposed to face the photodiodes of the second PD group; and a controller configured to extract biometric information of the subject based on the electrical signals generated by the plurality of photodiodes.

The body unit may include a first body and a second body which is disposed in parallel to the first body and is spaced apart from the first body; and each of the plurality of photodiodes has a first end connected to the first body and a second end connected to the second body.

The photodiodes of the first PD group may be disposed in a direction opposite to a direction in which the photodiodes of the second PD group are disposed.

The body unit may further include a third body which is disposed in parallel to and spaced apart from the first body or the second body; and the plurality of light emitting diodes may be mounted on the third body.

The body unit may include a first wire and a second wire which is disposed in parallel to the first wire and is spaced apart from the first wire. Each of the plurality of photodiodes has a first end connected to the first wire and a second end connected to the second wire. The photodiodes of the first PD group may be disposed in a direction opposite to a direction in which the photodiodes of the second PD group are disposed.

The plurality of light emitting diodes may be divided into a first light source group and a second light source group. The first light source group may be disposed corresponding to the first PD group. The second source group may be disposed corresponding to the second PD group.

The controller may be further configured to determine a number of the light emitting diodes of the first and second light source groups to controlled to be turned on or off.

The controller may be further configured to detect the electrical signals generated in the first PD group when the first light source group is operated, and detect the electrical signals generated in the second PD group when the second light source group is operated, and extract the biometric information of the subject based on a difference between the electrical signals detected in the first PD group and the second PD group.

The controller may be further configure to determine the number of the light emitting diodes based on a predetermined criterion which comprises at least one of a battery status, a type of data to be measured, and a measurement accuracy level of the wearable device.

The first PD group may be disposed on a first surface of the body unit, and the second PD group may be disposed on a second surface of the body unit. The first surface may be configured to be in contact with a back of a hand of the subject and the second surface may be configured to be in contact with a palm of the hand.

The controller may be further configured to generate a biomedical spectrum based on the electrical signals generated by the sensor and extract the biometric information of the subject which comprises at least one of skin temperature, skin color, and skin hydration degree based on the generated biomedical spectrum.

The controller may be further configured to determine whether the subject has a lesion based on the extracted biometric information of the subject.

The wearable device may further include an alarm unit configured to generate an alarm signal which includes at least one of an optical signal, a vibration signal, and a sound signal, in response to the controller determining that the subject has the lesion.

The wearable device may further include a display configured to display at least one of the biometric information of the subject and information on whether the subject has a lesion.

The sensor may further include temperature sensors configured to measure temperatures at two or more points on the subject.

The body unit may include at least two bodies, and the temperature sensors may be mounted on one of the bodies.

According to an aspect of another exemplary embodiment, there is provided a health monitoring method using a wearable device, the health monitoring method comprising: emitting light to a subject by at least one of a plurality of light emitting diodes included in the wearable device; receiving the light returning from the subject by a plurality of photodiodes included in the wearable device, the plurality of photodiodes being divided into a first photodiode (PD) group and a second PD group, the photodiodes in the first PD group being disposed to face the photodiodes of the second PD group; detecting electrical signals generated by the plurality of photodiodes based on the received light; and extracting biometric information of the subject based on the detected electrical signal.

The emitting he light may include determining, based on a predetermined criterion, a number of the light emitting diodes to be controlled to be turned on or off. The predetermined criterion may include at least one of a battery status, a type of data to be measured, and a measurement accuracy level of the wearable device.

The extracting the biometric information may include: generating a biomedical spectrum based on the electrical signals generated by the plurality of photodiodes; and extracting the biometric information of the subject which comprises at least one of skin temperature, skin color, and skin hydration degree based on the generated biomedical spectrum.

The health monitoring method may further include: measuring temperatures at two or more points on the subject by temperature sensors mounted in the wearable device; and extracting the biometric information of the subject based on the measured temperature.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
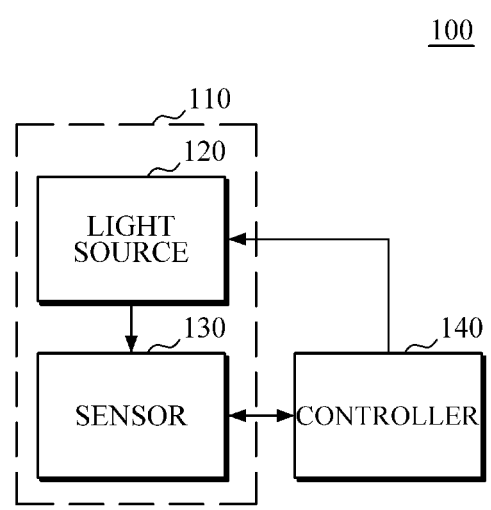
FIG. 1 is a block diagram illustrating one exemplary embodiment of a wearable device.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

The terms "comprises" and/or "comprising" as used herein will be understood to mean that an associated list is non-exhaustive and may or may not include any other additional suitable items, for example one or more further component(s), operation(s), procedure(s), and/or element(s) as appropriate. According to various exemplary embodiments of the present disclosure, the term "unit", means, but is not limited to, a software or hardware component, such as a field programmable gate array (FPGA) or application specific integrated circuit (ASIC), which performs certain tasks. A "unit" may advantageously be configured to reside on the addressable storage medium and configured to be executed on one or more processors.

Thus, a "unit" may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The components and the functionality provided for the units may be combined into fewer components and units or further separated into additional components and units.

FIG. 1 is a block diagram illustrating one exemplary embodiment of a wearable device.

Referring to FIG. 1, the wearable device 100 includes a body unit 110 and a controller 140. A light source 120 and a sensor 130 are mounted on the body unit 110.

The body unit 110 may allow the wearable device 100 to be worn on a human subject. For example, the body unit 110 may be in a band form that allows the wearable device 100 to be worn on the subject or may include a band connected thereto, wherein the band is in the form that may be worn around the subject. For example, the body unit 110 may be a ring (e.g., a smart ring), a watch (e.g., a smart watch), or a glove (e.g., a sensor-embedded glove).

The light source 120 may include a plurality of light emitting diodes, and the light emitting diodes may emit RGB light, RGBW light, infrared light, near-infrared light, etc. In addition, the wearable device 100 may use the light emitting diodes included in the light source 120 to emit light to a subject. For example, the light source 120 may include a fixing unit that fixes the light emitting diodes to the body unit 110 so as to emit light to the subject at a predetermined angle or include an angle adjustment unit that adjusts the angle at which the light emitting diodes emit light to the subject in response to a control signal of the controller 140.

The sensor 130 may include a plurality of photodiodes which convert light energy into electrical energy. For example, when light emitted from the light source 120 is reflected or scattered from a subject, the photodiodes of the sensor 130 may receive the light returning from the subject and generate electrical signals which are proportional to the intensity of the received light.

The photodiodes of the sensor 130 may be divided into a first photodiode (PD) group and a second PD group. The first PD group may be disposed in parallel to the second PD group on the body unit 110. For example, the body unit 110 may include a circuit in which two wires are disposed in parallel, and the photodiodes of the sensor 130 may be connected in parallel between the two wires. Meanwhile, the light emitting diodes of the light source 120 may be divided into a first light source group and a second light source group, wherein the light emitting diodes in the first light source group may be disposed corresponding to the photodiodes of the first PD group and the light emitting diodes in the second light source group may be disposed corresponding to the photodiodes of the second PD group.

In addition, the sensor 130 may include the same number of photodiodes as the number of light emitting diodes in the light source 120, and the light emitting diodes may be disposed in a one-to-one correspondence with the photodiodes. However, the present exemplary embodiment is not limited thereto, and the ratio of the number of photodiodes to the number of light emitting diodes may vary, for example, 3:1, 2:1, 1:2, and 1:3.

The photodiodes in the first PD group may be disposed on one surface of the body unit 110 which corresponds to the back of the subject's hand, and the photodiodes in the second PD group may be disposed on another surface of the body unit 110 which corresponds to the palm of the subject. For example, the photodiodes of the first PD group may be disposed at positions where the photodiodes may receive light returning from the back of the hand and the photodiodes of the second PD group may be disposed at positions where the photodiodes may receive light returning from the palm.

The controller 140 may detect electrical signals generated by the photodiodes and extract biometric information of the subject on the basis of the intensities of the detected electrical signals. Although FIG. 1 illustrates that the controller 140 is not included in the body unit 110, the exemplary embodiment is not limited thereto, and the controller 140 may be embedded in the body unit 110 or may be provided detachably from the outer circumference of the body unit 110. The controller 140 may include a processor and an execution memory, which are hardware, and include predefined program routines and/or a bus through which program data for the provision of specific functions of the terminal device is input to or output from a predetermined memory device, and a predetermined electrical circuit (or an integrated circuit) for the program routines and/or the bus. The controller 140 may be a generic term for program routines and/or program data which are software, loaded to the memory from a specific memory device and/or a chipset, and processed through the processor to perform specific functions. Various functions to be implemented in the wearable device 100 are realized, and the controller 140 may control and manage the overall operation of the wearable device 100 in order to implement functions described below.

The controller 140 may generate a biomedical spectrum based on the electrical signals generated by the photodiodes in the sensor 130 and extract biometric information of the subject based on the generated biomedical spectrum. For example, when the light source 120 sequentially emits green light, red light, yellow light, and blue light to the subject, the sensor 130 may sequentially generate electrical signals based on the light returning from the subject, and the controller 140 may generate a biomedical spectrum on the basis of the intensities of the electrical signals (e.g., voltage values) measured at an output terminal of the sensor 130. The photodiodes of the first PD group and the photodiodes of the second PD group are connected in parallel in different directions. Thus, when all the light emitting diodes of the light source 120 are turned on, the electrical signal generated in the sensor 130 may reflect a difference between the electrical signal generated by the photodiode of the first PD group and the electrical signal which is generated by the photodiode of the second PD group and has a direction opposite to that of the electrical signal generated by the photodiode of the first PD group.

In addition, the controller 140 may extract biometric information of the subject, such as skin temperature, skin color, or skin hydration degree, by applying a biomedical spectrum reconstruction algorithm to the biomedical spectrum generated by the sensor 130. Meanwhile, the controller 140 may extract a difference in skin temperature, a difference in skin color, a difference in skin hydration degree, and the like on the basis of the biomedical spectrum generated when all the light emitting diodes of the light source 120 are turned on.

The controller 140 may determine whether the subject has a lesion on the basis of the extracted biometric information of the subject. For example, the controller 140 may determine that the subject has drunk alcohol on the basis of information that the skin temperature of the subject is high and the skin color is redder than a predetermined reference. In another example, the controller 140 may determine that peripheral blood vessels of the subject have contracted on the basis of information that the skin color of the subject is pale and the skin temperature is lower than a reference temperature, or may determine that the peripheral blood vessels of the subject have expanded on the basis of information that the skin color of the subject is red and the skin temperature is higher than the reference temperature. In still another example, when a skin temperature difference, a skin color difference, or skin hydration degree difference between the back of the hand and the palm of the subject is greater than a reference value, the controller 140 may determine that there may be an abnormality (e.g., hyperhidrosis, body temperature imbalance, etc.) in the health of the subject. As described above, the wearable device 100 may identify the general health status of the subject on the basis of biometric information extractable from the hand of the subject and provide a health status monitoring service to the user.

In addition, the controller 140 may control some of or all the light emitting diodes of the first and second light source groups to be turned on/off according to a predetermined criterion. To this end, the controller 140 may determine the number of light emitting diodes to be controlled for turning on/off according to the predetermined criterion. Here, the predetermined criterion may be set based on a battery status, the purpose of measurement (e.g., type of data to be measured), measurement accuracy, or the like of the wearable device 100. For example, when the battery status is sufficient or accurate measurement is required according to the user's health status, the controller 140 may control all the light emitting diodes of the first light source group and the second light source group to be turned on. In this case, since various peak wavelengths may be obtained using a plurality of light emitting diodes having various light emission wavelengths, high-resolution spectral reconstruction is possible.

In another example, when remaining battery power of the wearable device 100 is lower than a reference value, the controller 140 may control only some of the light emitting diodes of the first light source group and the second light source group to be turned on. For example, a rate at which the light emitting diodes are turned on may be proportional to the remaining battery power. In another example, in the case in which it is intended to obtain an extraction result of biometric information of the subject based on infrared light, the controller 140 may control only the infrared light emitting diodes in the light source 120 to be turned on. In another example, in order to determine whether there is an abnormality in the subject's palm, the controller 140 may control only the light emitting diodes of the second light source group and the photodiodes of the second PD group that are disposed at positions corresponding to the palm of the subject to be turned on. For example, when an extracted color of the subject's palm is yellower than a predetermined reference, the controller 140 may determine that there is an abnormality in the liver or intestines of the subject. The extracted color may be represented by the combination of red, green, and blue (RGB) colors. The controller 140 may determine a red color proportion of the extracted color, and may determine that the extracted color is yellower than the predetermined reference if the red color proportion is greater than a reference red color proportion. In addition, the controller 140 may determine that there is an abnormality in the thyroid gland of the subject on the basis of information that the skin hydration degree and skin temperature of the palm of the subject are higher than reference values.

Alternatively, the controller 140 may separate the first light source group from the second light source group and sequentially control the groups. When the first light source group is operated, the controller 140 may detect electrical signals generated in the first PD group, and when the second light source group is operated, the controller 140 may detect electrical signals generated in the second PD group. Also, the controller 140 may generate the biomedical spectrum by calculating differences between the detected electrical signals and may extract biometric information of the subject by applying the biomedical spectrum reconstruction algorithm to the generated biomedical spectrum. Here, the biomedical spectrum reconstruction algorithm is an algorithm which allows the extraction of biomedical information, such as temperature, color, hydration degree, and the like, by use of the biomedical spectrum.

As described above, by using a method in which the biomedical spectrum is generated based on the electrical signals generated by the sensor 130 when the light emitting diodes of the first light source group and the second light source group are simultaneously turned on and a method in which the biomedical spectrum is generated by detecting each electrical signal generated by the sensor 130 when the light emitting diodes of each of the first light source group and the second light source group are turned on and calculating the differences between the detected electrical signals, the controller 140 may generate the biomedical spectrum to be used for extracting biometric information of the subject.

In addition, the wearable device 100 may further include a database in which the biometric information, such as temperature, color, hydration degree, etc., extracted by the controller 140, and additional information of the subject are stored. For example, additional information, such as the tension state of the subject, whether the subject has consumed alcohol, blood circulation information, etc., may be stored in the database at the time of extracting the biometric information of the subject, and the biometric information and the additional information may be matched to be stored in the database. In addition, personal information of the subject, the medical history and treatment history of the subject, exercise performance, comprehensive analysis information, and the like may be further stored in the database. On the other hand, the controller 140 may train the biomedical spectrum reconstruction algorithm using the biometric information and additional information of the subject stored in the database, thereby making it possible to improve the accuracy and efficiency of biometric information extraction and determination as to whether the subject has a lesion.

Figure 2:
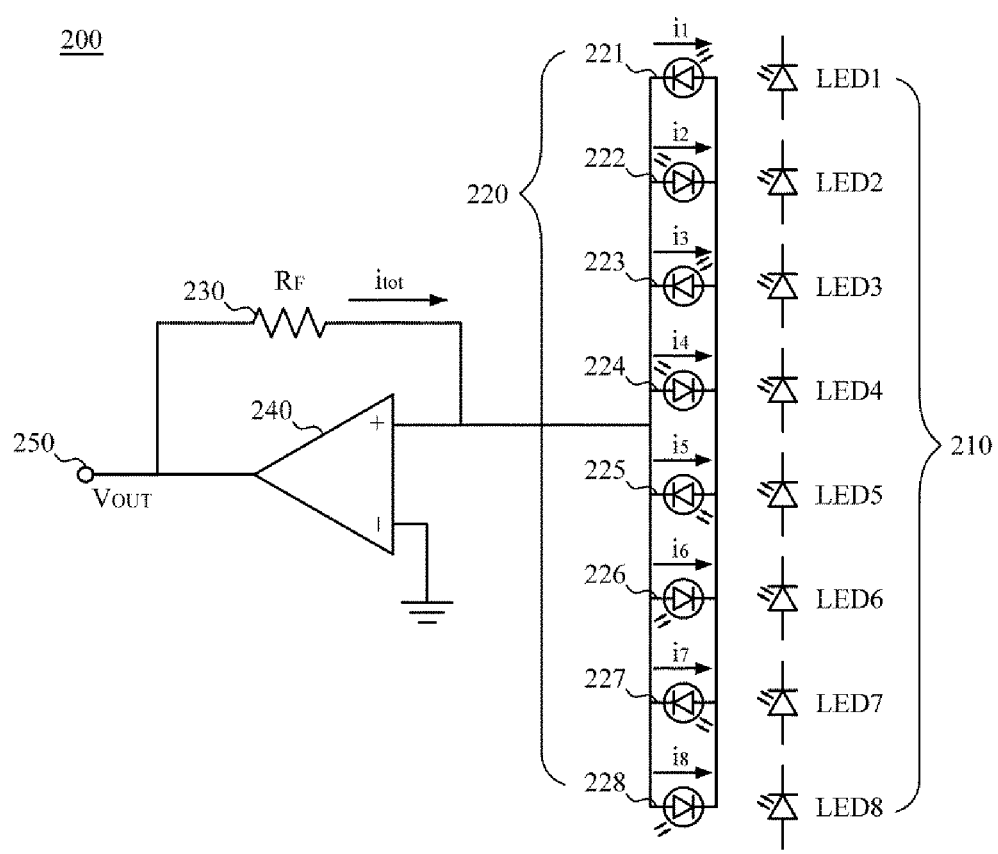
FIG. 2 is a diagram for describing a wearable device in terms of a circuit.

FIG. 2 is a diagram for describing a wearable device in terms of a circuit.

Referring to FIG. 2, the wearable device 200 includes a plurality of light emitting diodes 210, a plurality of photodiodes 220, a resistor 230, an operational amplifier 240, and an output terminal 250. Although it is illustrated that the wearable device 200 has eight light emitting diodes LED1 to LED8 and eight photodiodes 221 to 228 in FIG. 2, this is merely for convenience of descriptions, and the numbers of light emitting diodes 210 and the photodiodes 220 included in the wearable device 200 are not limited thereto.

The photodiodes 220 may be connected in parallel as shown in FIG. 2. A direction in which a flow of current due to electrical signals generated by the photodiodes 220 may be determined based on orientations of the anode and cathode of each photodiode 220. For example, as shown in FIG. 2, the photodiodes 221, 223, 225, and 227 whose anodes are oriented to the right generate electrical signals so that a current flows to the right and the photodiodes 222, 224, 226, and 228 whose anodes are oriented to the left generate electrical signals so that a current flows to the left. In addition, as described above, the photodiodes 220 may be divided into a first PD group and a second PD group. For example, in FIG. 2, the photodiodes 221, 223, 225, and 227 whose anodes are oriented to the right may be classified as the first PD group and the photodiodes 222, 224, 226, and 228 whose anodes are oriented to the left may be classified as the second PD group.

The light emitting diodes 210 may be divided into a first light source group LED1, LED3, LED5, and LED7 and a second light source group LED2, LED4, LED6, and LED8. The light emitting diodes LED1, LED3, LED5, and LED7 in the first light source group may be disposed at positions corresponding to the photodiodes 221, 223, 225, and 227 of the first PD group and the light emitting diodes LED2, LED4, LED6, and LED8 in the second light source group may be disposed at positions corresponding to the photodiodes 222, 224, 226, and 228 of the second PD group. In this case, the light emitting diodes LED1 and LED2 may be green light-emitting diodes, the light emitting diodes LED3 and LED4 may be red light-emitting diodes, the light emitting diodes LED5 and LED6 may be yellow light-emitting diodes, and the light emitting diodes LED7 and LED8 may be blue light-emitting diodes.

Although it is shown that the light emitting diodes 210 are disposed in a one-to-one correspondence with the photodiodes 220 in FIG. 2, the arrangement is not limited thereto, and the ratio of the number of photodiodes 220 to the number of light emitting diodes 210 may vary, for example, 3:1, 2:1, 1:2, and 1:3.

The resistor 230 and the operational amplifier 240 may amplify the electrical signals generated by the photodiodes 220, and the amplified electrical signals may be output through the output terminal 250. As shown in Equation 1 below, a voltage value $V_{out}$ corresponding to a value obtained by multiplying the sum $i_{tot}$ of currents generated in the photodiodes 220 by the magnitude $R_F$ of the resistor 230 may be output to the output terminal 250. In this case, the output voltage may be used in extracting biometric information of a subject.

$$V_{out} = i_{tot} \times R_F \qquad \text{[Equation 1]}$$

Meanwhile, an output voltage value at the output terminal 250 when all the light emitting diodes 210 are turned on may be obtained using Equation 2 below.

$$V_{out} = (i_1 - i_2 + i_3 - i_4 + i_5 - i_6 + i_7 - i_8) \times R_F \qquad \text{[Equation 2]}$$

In Equation 2, minus symbols (−) in front of $i_2$, $i_4$, $i_6$, and $i_8$ indicate that an actual direction of current flow is opposite to a direction of $i_2$, $i_4$, $i_6$, and $i_8$ because currents due to the electrical signals generated in the photodiodes 222, 224, 226, 228 whose anodes are oriented to the left flow to the left.

Figure 3:
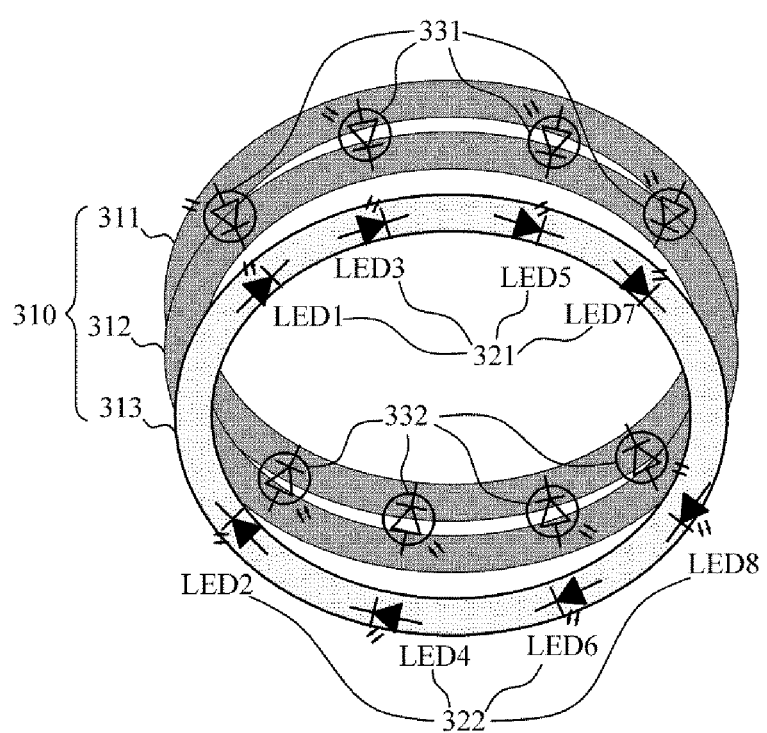
FIG. 3 is a diagram illustrating one exemplary embodiment of a body unit, a light source, and a sensor.

FIG. 3 is a diagram illustrating one exemplary embodiment of a body unit, a light source, and a sensor.

Referring to FIG. 3, the body unit 310 may be in the form of a ring that may be worn around a finger. For example, the body unit 310 may be made of an elastic material so that the body unit 310 may be fitted to any finger regardless of the thickness of the finger. Alternatively, only a part of the body unit may be made of an elastic material.

The body unit 310 may include a first body 311 and a second body 312 which are disposed in parallel and spaced apart from each other. For example, the body unit 310 may include the first body 311 and the second body 312 in the form of a ring as shown in FIG. 3, and the first body 311 and the second body 312 may be fixed to each other or detachable from each other.

Each of the photodiodes 331 and 332 may have one end connected to the first body 311 and the other end connected to the second body 312. Since the photodiodes 331 and 332 each have one end connected to the first body 311 and the other end connected to the second body 312, a circuit may be implemented in which the plurality of photodiodes 331 and 332 are connected in parallel. In addition, the photodiodes 331 and 332 may be fixed to or detachable from the first body 311 and the second body 312.

The photodiode 331 of a first PD group and the photodiode 332 of a second PD group of a sensor may be disposed in opposite directions in the body unit 310. For example, when the cathode of the photodiode 331 of the first PD group is connected to the first body 311 and the anode thereof is connected to the second body 312, the cathode of the photodiode 332 of the second PD group may be connected to the second body 312 and the anode may be connected to the first body 311. Alternatively, when the cathode of the photodiode 331 of the first PD group is connected to the second body 312 and the anode thereof is connected to the first body 311, the cathode of the photodiode 332 of the second PD group may be connected to the first body 311 and the anode may be connected to the second body 312.

The body unit 310 may further include a third body 313 which is disposed in parallel to and spaced apart from the first body 311 or the second body 312. The light emitting diodes 321 and 322 of the sensor may be mounted on the third body 313. For example, the third body 313 may be fixed to or detachable from the first body 311 and the second body 312. In addition, the third body 313 may include a coupling unit which is coupled to the first body 311 or the second body 312 only when the first body 311 and the second body 312 are engaged with each other so that the light emitting diode 321 of the first light source group is disposed corresponding to the photodiode 331 of the first PD group and the light emitting diode 322 of the second light source group is disposed corresponding to the photodiode 332 of the second PD group.

The photodiodes 331 and 332 and the light emitting diodes 321 and 322 may be provided on an inside surface of the body unit 310 so as to directly receive light returning from a subject. For example, the body unit 310 may include a light shielding unit which shields light emitted from a light source other than the light emitting diodes 321 and 322 when the body unit 310 is put on the subject, so that an error which may occur due to the light radiated from a light source, other than the light emitting diodes 321 and 322, during the extraction of biometric information of the subject may be reduced.

Referring to FIGS. 1 to 3, the controller 140 may generate the biomedical spectrum on the basis of an output voltage value at the output terminal 250. As described above, the controller 140 may control all or some of the light emitting diodes 321 and 322 of the first light source group and the second light source group to be turned on/off. For example, when the photodiodes 331 and 332 are disposed as shown in FIG. 3, the controller 140 may detect a voltage value $V_{o1}$ at the output terminal 250 when the light emitting diodes LED1 and LED2 are turned on, detect a voltage value $V_{o2}$ at the output terminal 250 when the light emitting diodes LED3 and LED4 are turned on, detect a voltage value $V_{o3}$ at the output terminal 250 when the light emitting diodes LED5 and LED6 are turned on, and detect a voltage value $V_{o4}$ at the output terminal 250 when the light emitting diodes LED7 and LED8 are turned on. The above voltage values may be calculated by Equations 3 to 6 below.

$$V_{o1}=(i_1-i_2)\times R_F \quad \text{[Equations 3]}$$

$$V_{o2}=(i_3-i_4)\times R_F \quad \text{[Equations 4]}$$

$$V_{o3}=(i_5-i_6)\times R_F \quad \text{[Equations 5]}$$

$$V_{o4}=(i_7-i_8)\times R_F \quad \text{[Equations 6]}$$

The controller 140 may generate a biomedical spectrum on the basis of the calculated voltage values $V_{o1}$ to $V_{o4}$ at the output terminal 250 and extract the biometric information of the subject using the generated biomedical spectrum so as to determine whether the subject has a lesion.

In addition, the controller 140 may detect each output voltage value at the output terminal 250 when each of the light emitting diodes LED1 to LED8 is turned on and may extract the biometric information of the subject on the basis of the detected voltage values.

For example, the controller 140 may generate a biomedical spectrum on the basis of voltage values, each of which is output from the output terminal 250 when each of the light emitting diodes LED1, LED3, LED5, and LED7 disposed at positions corresponding to the back of the subject's hand is turned on, and may extract biometric information related to the back of the subject's hand on the basis of the biomedical spectrum. Also, the controller 140 may generate a biomedical spectrum on the basis of voltage values, each of which is output from the output terminal 250 when each of the light emitting diodes LED2, LED4, LED6, and LED8 disposed at positions corresponding to the subject's palm is turned on, and may extract biomedical information related to the subject's palm on the basis of the generated biomedical spectrum.

In another example, the controller 140 may generate a biomedical spectrum on the basis of voltage values, each of which is output from the output terminal 250 when each of the light emitting diodes LED1, LED3, LED5, and LED7 disposed at positions corresponding to the back of the subject's hand is turned on, generate a biomedical spectrum on the basis of voltage values, each of which is output from the output terminal 250 when each of the light emitting diodes LED2, LED4, LED6, and LED8 disposed at positions corresponding to the subject's palm is turned on, and extract a difference in skin temperature, a difference in skin color, a difference in skin hydration degree, etc. between the back of the hand and the palm of the subject by calculating a difference between the generated two biomedical spectra.

Figure 4:
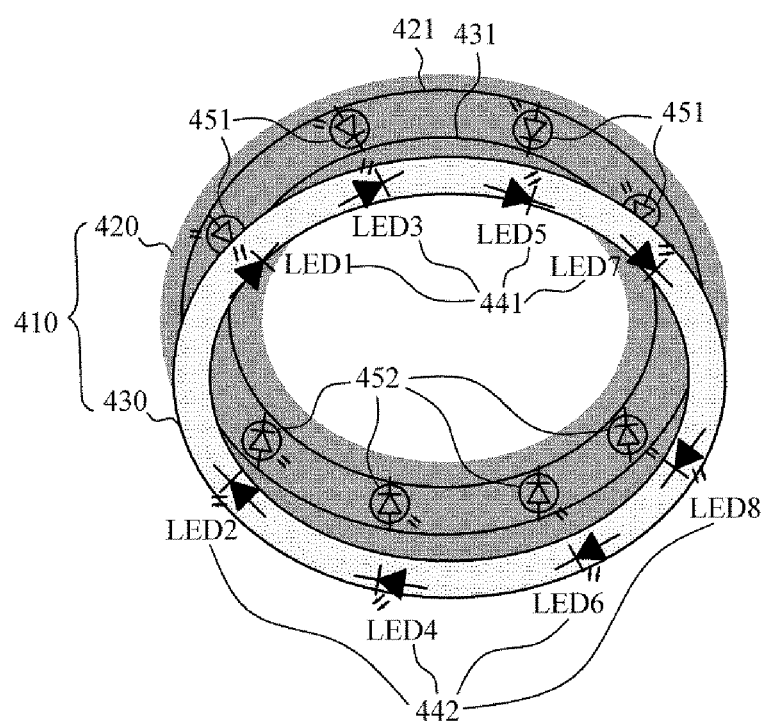
FIG. 4 is a diagram illustrating another exemplary embodiment of a body unit, a light source, and a sensor.

FIG. 4 is a diagram illustrating another exemplary embodiment of a body unit, a light source, and sensor.

Referring to FIG. 4, the body unit 410 may be in the form of a ring that may be worn around a finger. The body unit 410 may include at least two bodies 420 and 430. One of the bodies may include a first wire 421 and a second wire 431 which are disposed in parallel and spaced apart from each other.

A plurality of photodiodes 451 and 452 of a sensor may each have one end connected to the first wire 421 and the other end connected to the second wire 431 so that a circuit may be implemented in which the plurality of photodiodes 451 and 452 are connected in parallel.

The photodiode 451 of a first PD group and the photodiode 452 of a second PD group of the sensor may be disposed in opposite directions. For example, when the cathode of the photodiode 451 of the first PD group is connected to the first wire 421 and the anode thereof is connected to the second wire 431, the cathode of the photodiode 452 of the second PD group may be connected to the second wire 431 and the anode thereof may be connected to the first wire 421. Alternatively, when the cathode of the photodiode 451 of the first PD group is connected to the second wire 431 and the anode thereof is connected to the first wire 421, the cathode of the photodiode 452 of the second PD group may be connected to the first wire 421 and the anode thereof may be connected to the second wire 431.

In addition, the other body 430 may be disposed in parallel to and spaced apart from the body 420, and light emitting diodes 441 and 442 of the sensor may be mounted on the other body 430. For example, the other body 430 may be fixed to or detachable from the body 420.

Figure 5:
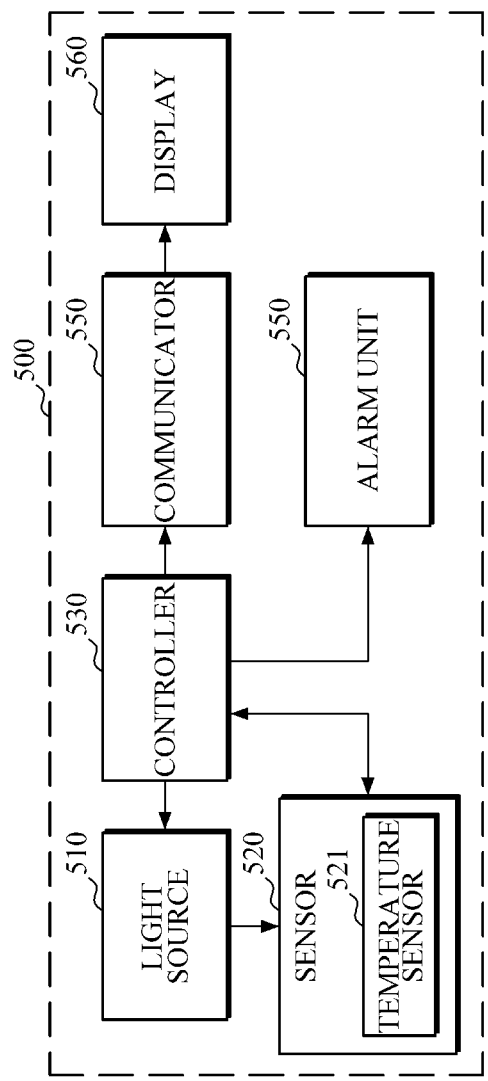
FIG. 5 is a block diagram illustrating another exemplary embodiment of a wearable device.

FIG. 5 is a block diagram illustrating another exemplary embodiment of a wearable device.

Referring to FIG. 5, a wearable device 500 includes a light source 510, a sensor 520, a controller 530, an alarm unit 540, a communicator (e.g., communication interface) 550, and a display 560, and the sensor 520 may include a temperature sensor 521. Since the light source 510, the sensor 520, and the controller 530 are described with reference to FIG. 1, the detailed descriptions thereof will be omitted.

The sensor 520 may include a plurality of temperature sensors 521 which measure a temperature at two or more points. The two points may be the back of a hand and palm of a subject.

The alarm unit 540 may generate an alarm signal on the basis of whether the subject has a lesion or not. For example, the alarm signal may include an optical signal, a vibration signal, a sound signal, etc. In addition, the alarm unit 540 may generate different alarm signals according to the degree of the lesion of the subject. For example, the alarm unit 540 may generate an optical signal whose color becomes reddish as the degree of the lesion of the subject increases and generate an optical signal whose color becomes greenish as the degree of the lesion decreases. In other example, the alarm unit 540 may generate a pre-recorded voice of a person informing the subject of the abnormality in the health status or a software-generated voice reading text, as an alarm signal, or may generate a sound effect, such as an alarm sound, an emergency bell sound, or a short piece of music.

For example, the alarm unit 540 may further include an alarm light which visualizes an optical signal, a vibration device which generates vibrations, a speaker which provides a sound signal, and the like. In other example, the alarm signal generated by the alarm unit 540 may provide the user with an alarm signal from a device placed a predetermined distance from the body unit through the communicator 550.

The display 560 may display information related to the subject's health, such as biometric information of the subject, whether the subject has a lesion or not, and the like. For example, the display 560 may be a display device having a size suitable to be attached on the body unit, or a display device attached to a terminal device in the shape of a watch (e.g., a smart watch). In addition, the display 560 may visually provide the alarm signal generated by the alarm unit 540.

The communicator 550 may perform wireless communication with an external electronic device. For example, the communicator 550 may include various network protocols, such as cable Internet, wireless Internet, infrared communication, Bluetooth, wideband code division multiple access (WCDMA), wireless broadband (WiBro), wireless-fidelity (Wi-Fi), long term evolution (LTE), LTE-advanced (LTE-A), a wired/wireless telephone network, etc. in order to implement the communication function.

The sensor 520 may further include the temperature sensors 521 which measure a temperature at two or more points on the subject.

The body unit includes at least two or more bodies, in one of which the temperature sensors 521 may be mounted. For example, the body having the temperature sensors 521 may be fixed to or detachable from the other body.

The controller 530 may calculate a difference in temperature between the two or more points on the subject through the temperature sensors 521 and extract biometric information of the subject or determine whether the subject has a lesion on the basis of the calculated difference in temperature. In addition, the controller 530 may extract the biometric information of the subject or determine whether the subject has a lesion by taking into account both a biomedical spectrum generated using the light emitting diodes of the light source 510 and the photodiodes of the sensor 520 and the difference in temperature calculated using the temperature sensors 521.

Figure 6:
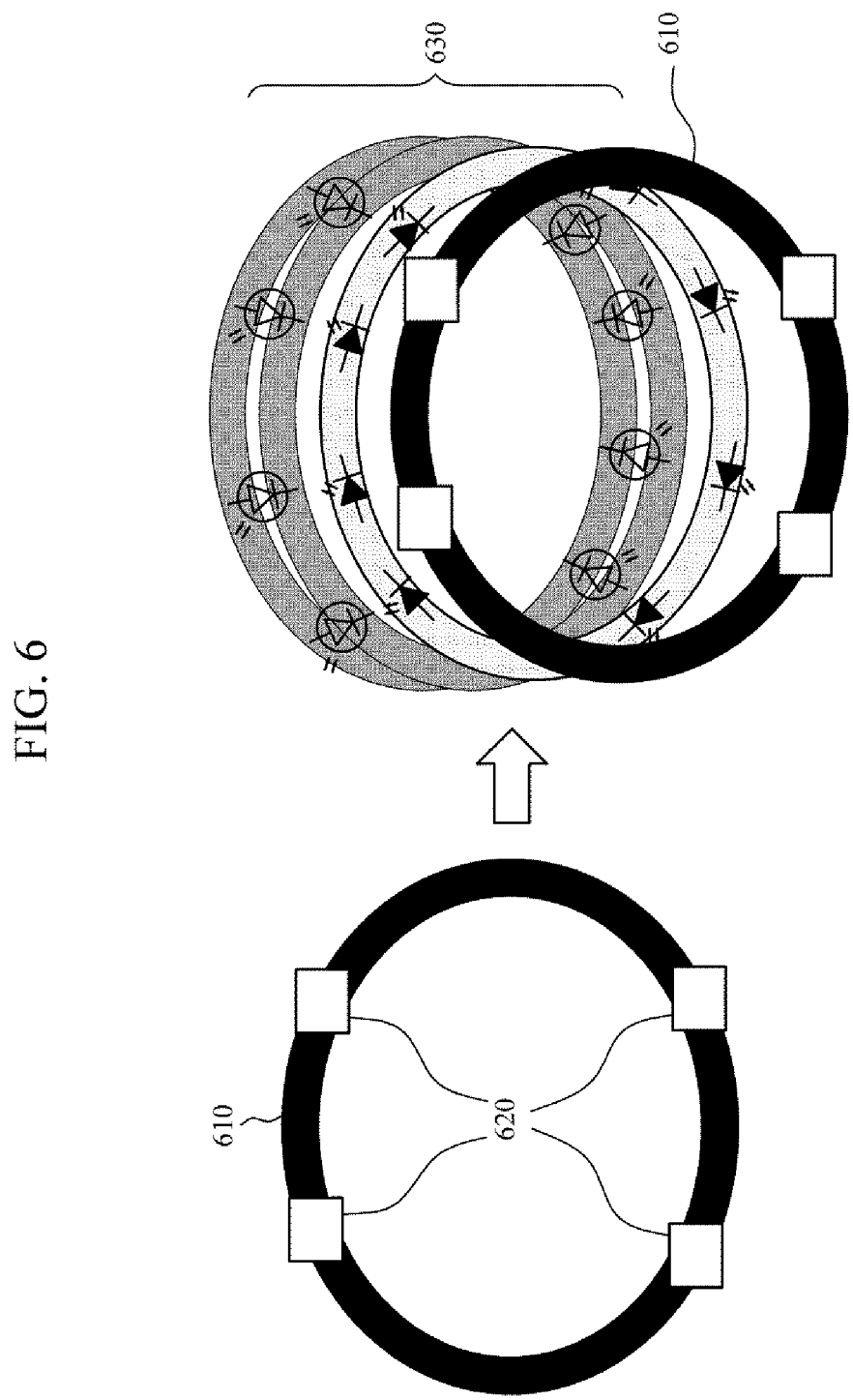
FIG. 6 is a diagram illustrating one exemplary embodiment of a wearable device including two or more temperature sensors.

FIG. 6 is a diagram illustrating one exemplary embodiment of a wearable device including two or more temperature sensors.

Referring to FIG. 6, a plurality of temperature sensors 620 may be provided to measure temperatures at two or more points on a subject, and as shown in FIG. 6, the temperature sensors 620 may be mounted on a body 610. In addition, some temperature sensors 620 may be disposed at positions corresponding to the back of the hand of the subject, and the remaining temperature sensors 620 may be disposed at positions corresponding to the palm of the subject, so that the temperatures at the back of the hand and the palm can be measured.

In addition, the body 610 including the temperature sensors 620 may be directly or indirectly connected with another body of a body unit 630, as shown in the right part of FIG. 6. For example, a body of the body unit 630 and the body 610 on which the temperature sensors 620 are mounted may be physically and directly connected with each other, or alternatively, the body unit 630 and the body 610 on which the temperature sensors are mounted may be worn on the same or different fingers of the subject so that the body unit 630 and the body 610 may be connected with each other and exchange information through near field communication, such as radio frequency identification (RFID), infrared communication, or the like.

Figure 7:
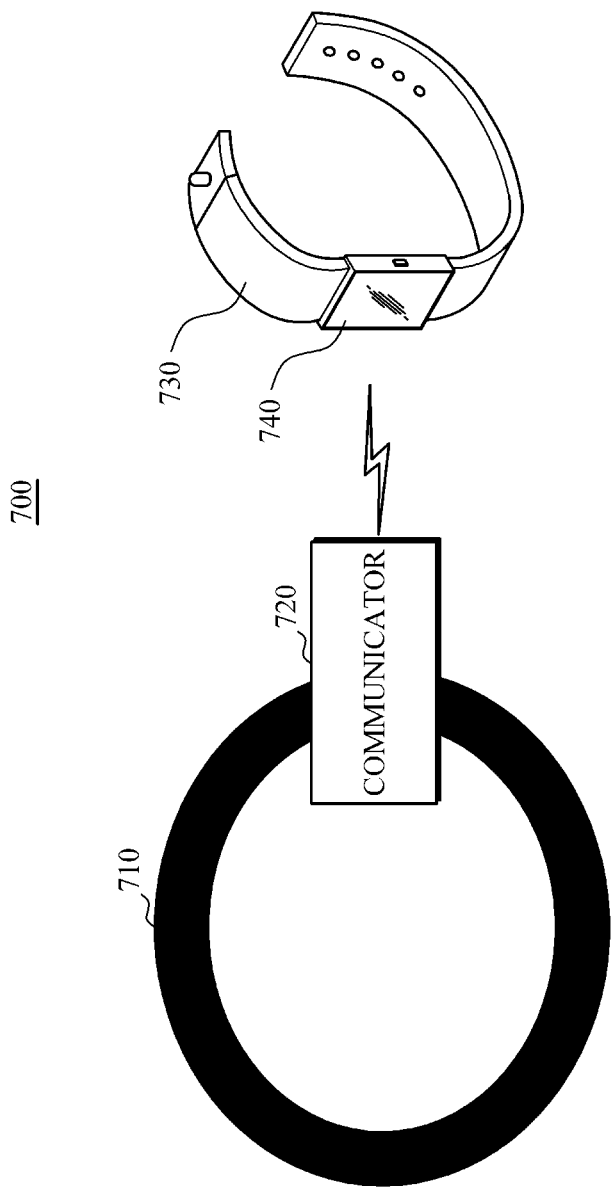
FIG. 7 is a diagram illustrating one exemplary embodiment of a wearable device including a communicator.

FIG. 7 is a diagram illustrating one exemplary embodiment of a wearable device including a communicator.

Referring to FIG. 7, a wearable device 700 includes a body unit 710 and an external electronic device 730. For example, the body unit 710 may include a communicator 720 which performs wireless communication with the external electronic device 730, and the external electronic device 730 may include a display 740 which displays biometric information of a subject, whether the subject has a lesion, or the like.

As such, the wearable device 700 may display the biometric information of the subject or information on whether the subject has a lesion, which is extracted by the body unit 710, on the display 740 provided in the external electronic device 730.

The external electronic device 730 may be a smart watch worn around the wrist of the subject as shown in FIG. 7, or may be a specific terminal device, such as a desktop computer, a notebook computer, a smartphone, a personal digital assistant, a mobile phone, a game console, etc., which may collect, analyze, process, store, and display data.

Figure 8:
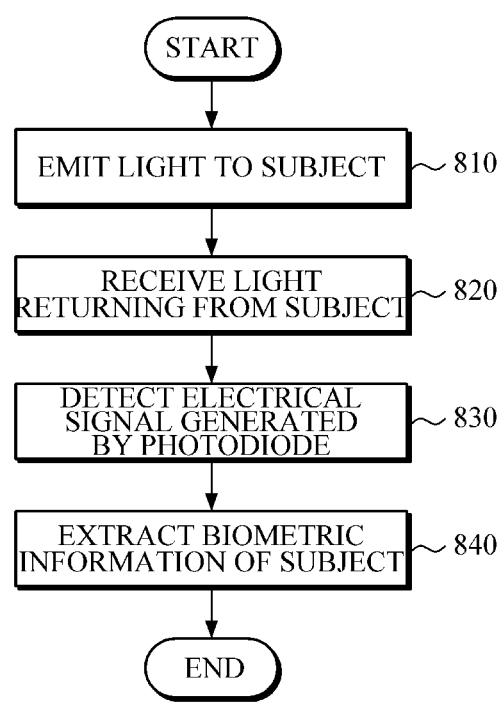
FIG. 8 is a flowchart illustrating one exemplary embodiment of a health monitoring method.

FIG. 8 is a flowchart illustrating one exemplary embodiment of a health monitoring method.

Referring to FIGS. 1 and 8, the wearable device 100 emits light to a subject using a plurality of light emitting diodes (operation 810).

The wearable device 100 receives light returning from the subject using a plurality of photodiodes which are divided into the first PD group and the second PD group and disposed in parallel on the body unit (operation 820). The photodiodes may convert light energy into electrical energy. In addition, the wearable device 100 may control some of or all the light emitting diodes of the first and second light source groups to be turned on/off according to a predetermined criterion which includes a battery status, the purpose of measurement, measurement accuracy, or the like of the wearable device 100. The photodiodes of the first PD group and the photodiodes of the second PD group may be disposed in opposite directions. In one example, when the cathode of each photodiode of the first PD group is connected to a first body of the body unit and the anode thereof is connected to a second body, the cathode of each photodiode of the second PD group may be connected to the second body and the anode thereof may be connected to the first body. In another example, when the cathode of each photodiode of the first PD group is connected to the second body and the anode thereof is connected to the first body, the cathode of each photodiode of the second PD group may be connected to the first body and the anode thereof may be connected to the second body. In still another example, the cathode of each photodiode of the first PD group is connected to a first wire and the anode thereof is connected to a second wire, or the cathode of each photodiode of the second PD group may be connected to the second wire and the anode thereof may be connected to the first wire.

The wearable device 100 detects electrical signals generated by the plurality of photodiodes on the basis of the received light (operation 830). For example, when light emitted to the subject returns from the subject, the photodiodes may each receive the light returning from the subject and generate an electrical signal which is proportional to the intensity of the received light.

The wearable device 100 extracts biometric information of the subject on the basis of the detected electrical signals (operation 840). The biometric information of the subject may include skin temperature, skin color, skin hydration degree, etc.

Figure 9:
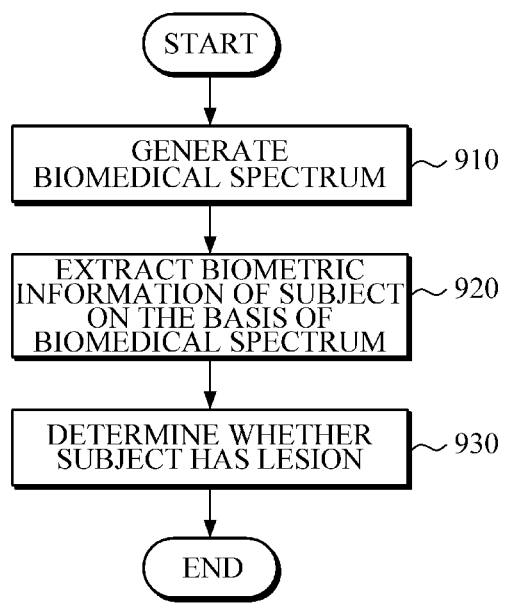
FIG. 9 is a flowchart illustrating another exemplary embodiment of a health monitoring method.

FIG. 9 is a flowchart illustrating another exemplary embodiment of a health monitoring method.

Referring to FIGS. 1 and 9, the wearable device 100 generates a biomedical spectrum on the basis of electrical signals generated by a plurality of photodiodes (operation 910), and extracts biometric information of a subject on the basis of the generated biomedical spectrum (operation 920). More specifically, the wearable device 100 may sequentially emit green light, red light, yellow light, and blue right to the subject, sequentially generate electrical signals on the basis of light returning from the subject, and generate a biomedical spectrum on the basis of intensities of sequentially generated electrical signals. Meanwhile, since the photodiodes of the first PD group and the photodiodes of the second PD group of the wearable device 100 are disposed in parallel and in different directions, the electrical signal generated by the wearable device 100 is based on a difference between the electrical signal generated by the photodiode of the first PD group and the electrical signal generated in an opposite direction by the photodiode of the second PD group.

The wearable device 100 determines whether the subject has a lesion on the basis of the extracted biometric information of the subject (operation 930). In one example, the wearable device 100 may determine that the subject has hyperhidrosis on the basis of information that the skin hydration degree and the skin temperature of the subject are high, or may determine that the subject has drunk alcohol on the basis of information that the skin temperature of the subject is high and the skin color of the subject is redder than a predetermined reference. In another example, the wearable device 100 may determine that the peripheral blood vessels of the subject have contracted on the basis of information that the skin color of the subject is pale and the skin temperature is lower than a reference value, or may determine that the peripheral blood vessels of the subject have expanded on the basis of information that the skin color of the subject is red and the skin temperature is higher than the reference value. As such, the wearable device 100 may determine the overall health status of the subject on the basis of biometric information extracted from the hand of the subject, thereby providing a health status monitoring service to the user.

Figure 10:
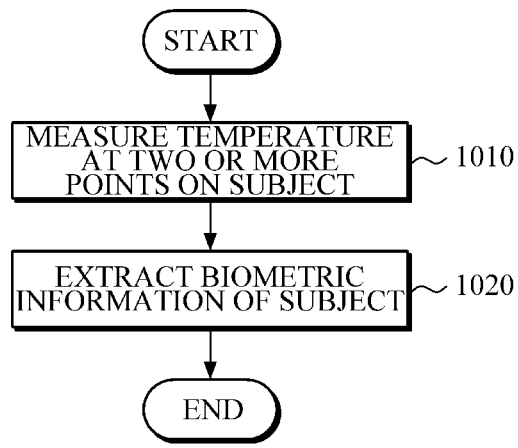
FIG. 10 is a flowchart illustrating another exemplary embodiment of a health monitoring method.

FIG. 10 is a flowchart illustrating another exemplary embodiment of a health monitoring method.

Referring to FIGS. 5 and 10, the wearable device 500 measures temperatures at two or more points on a subject using a plurality of temperature sensors (operation 1010).

The wearable device 500 extracts biometric information of the subject on the further basis of the measured temperatures (operation 1020). The wearable device 500 may calculate a difference in temperature between the two or more points on the subject through the temperature sensors 521 and extract biometric information of the subject or determine whether the subject has a lesion on the basis of the calculated difference in temperature. For example, the wearable device 500 may measure temperatures at the back of the hand and the palm of the subject, calculate a difference between the measured temperatures, and may determine that there may be an abnormality in the health status of the subject when the calculated difference is greater than a reference value. In addition, the wearable device 500 may extract the biometric information of the subject or determine whether the subject has a lesion by taking into account both a biomedical spectrum generated using the light emitting diodes and the photodiodes and the difference in temperature calculated using the temperature sensors.

While not restricted thereto, an exemplary embodiment can be embodied as computer-readable code on a computer-readable recording medium. The computer-readable recording medium is any data storage device that can store data that can be thereafter read by a computer system.

Examples of the computer readable recording medium include a read only memory (ROM), a read access memory (RAM), a compact disk-ROM (CD-ROM), a magnetic tape, a floppy disk, and an optical disc. Further, the record medium may be implemented in the form of a carrier wave such as Internet transmission. In addition, the computer readable recording media may be distributed in computer systems over a network, in which computer readable code may be stored and executed in a distributed manner. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A wearable device comprising:
a body unit configured to be worn on a subject;
a light source comprising a plurality of light emitting diodes configured to emit light to the subject;
a sensor comprising a plurality of photodiodes disposed on the body unit and configured to generate electrical signals based on the light returning from the subject, the plurality of photodiodes being divided into a first photodiode (PD) group and a second PD group, and the photodiodes of the first PD group being disposed to face the photodiodes of the second PD group; and
a controller configured to extract biometric information of the subject based on the electrical signals generated by the plurality of photodiodes, wherein:
the body unit comprises a first body and a second body which is disposed in parallel to the first body and is spaced apart from the first body; and
each of the plurality of photodiodes has a first end connected to the first body and a second end connected to the second body.

2. The wearable device of claim 1, wherein the photodiodes of the first PD group are disposed in a direction opposite to a direction in which the photodiodes of the second PD group are disposed.

3. The wearable device of claim 1, wherein:
the body unit further comprises a third body which is disposed in parallel to and spaced apart from the first body or the second body; and
the plurality of light emitting diodes are mounted on the third body.

4. The wearable device of claim 1, wherein:
the body unit comprises a first wire and a second wire which is disposed in parallel to the first wire and is spaced apart from the first wire;
each of the plurality of photodiodes has the first end connected to the first wire and the second end connected to the second wire; and
the photodiodes of the first PD group are disposed in a direction opposite to a direction in which the photodiodes of the second PD group are disposed.

5. The wearable device of claim 1, wherein:
the plurality of light emitting diodes are divided into a first light source group and a second light source group;
the first light source group is disposed corresponding to the first PD group; and
the second source group is disposed corresponding to the second PD group.

6. The wearable device of claim 5, wherein the controller is further configured to determine a number of the light emitting diodes of the first and second light source groups to controlled to be turned on or off.

7. The wearable device of claim 6, wherein when the controller is further configured to detect the electrical signals generated in the first PD group when the first light source group is operated, and detect the electrical signals generated in the second PD group when the second light source group is operated, and extract the biometric information of the subject based on a difference between the electrical signals detected in the first PD group and the second PD group.

8. The wearable device of claim 6, wherein the controller is further configure to determine the number of the light emitting diodes based on a predetermined criterion which comprises at least one of a battery status, a type of data to be measured, and a measurement accuracy level of the wearable device.

9. The wearable device of claim 1, wherein:
the first PD group is disposed on a first surface of the body unit and the second PD group is disposed on a second surface of the body unit, and
the first surface is configured to be in contact with a back of a hand of the subject and the second surface is configured to be in contact with a palm of the hand.

10. The wearable device of claim 1, wherein the controller is further configured to generate a biomedical spectrum based on the electrical signals generated by the sensor and extract the biometric information of the subject which comprises at least one of skin temperature, skin color, and skin hydration degree based on the generated biomedical spectrum.

11. The wearable device of claim 10, wherein the controller is further configured to determine whether the subject has a lesion based on the extracted biometric information of the subject.

12. The wearable device of claim 11, further comprising an alarm unit configured to generate an alarm signal which comprises at least one of an optical signal, a vibration signal, and a sound signal, in response to the controller determining that the subject has the lesion.

13. The wearable device of claim 12, further comprising a display configured to display at least one of the biometric information of the subject and information on whether the subject has the lesion.

14. The wearable device of claim 1, wherein the sensor further comprises temperature sensors configured to measure temperatures at two or more points on the subject.

15. The wearable device of claim 14, wherein the body unit comprises at least two bodies, and the temperature sensors are mounted on one of the bodies.

16. A health monitoring method using a wearable device, the health monitoring method comprising:
emitting light to a subject by at least one of a plurality of light emitting diodes included in the wearable device;
receiving the light returning from the subject by a plurality of photodiodes disposed on a body unit of the wearable device, the plurality of photodiodes being divided into a first photodiode (PD) group and a second PD group, the photodiodes in the first PD group being disposed to face the photodiodes of the second PD group, the body unit including a first body and a second body which is disposed in parallel to the first body and is spaced apart from the first body, and each of the plurality of photodiodes having a first end connected to the first body and a second end connected to the second body;

detecting, using a controller included in the wearable device, electrical signals generated by the plurality of photodiodes based on the received light; and extracting, using the controller, biometric information of the subject based on the detected electrical signals.

17. The health monitoring method of claim 16, wherein the emitting the light comprises determining, based on a predetermined criterion, a number of the light emitting diodes to be controlled to be turned on or off, and wherein the predetermined criterion comprises at least one of a battery status, a type of data to be measured, and a measurement accuracy level of the wearable device.

18. The health monitoring method of claim 16, wherein the extracting the biometric information comprises:

generating a biomedical spectrum based on the electrical signals generated by the plurality of photodiodes; and extracting the biometric information of the subject which comprises at least one of skin temperature, skin color, and skin hydration degree based on the generated biomedical spectrum.

19. The health monitoring method of claim 16, further comprising:

measuring temperatures at two or more points on the subject by temperature sensors mounted in the wearable device; and extracting the biometric information of the subject based on the measured temperature.

* * * * *